(12) United States Patent
Chan

(10) Patent No.: US 7,311,931 B2
(45) Date of Patent: Dec. 25, 2007

(54) HERBAL PREPARATION FOR JOINTS

(75) Inventor: Hei Ling Helen Chan, Tregunter Path (HK)

(73) Assignee: Vita Green Health Products Co., Ltd., Hong Kong SAR (HK)

( * ) Notice: Subject to any disclaimer, the term of this patent is extended or adjusted under 35 U.S.C. 154(b) by 301 days.

(21) Appl. No.: 11/023,817

(22) Filed: Dec. 28, 2004

(65) Prior Publication Data

US 2006/0141062 A1     Jun. 29, 2006

(51) Int. Cl.
*A61K 36/00*     (2006.01)

(52) U.S. Cl. ..................................... 424/774

(58) Field of Classification Search ............. None
See application file for complete search history.

(56) References Cited

OTHER PUBLICATIONS

Cheng Y-X, Zhou J and Tan N-H (2001) Journal of integrative Plant Biology (Acta Botanica Sinica) 43(7):760-765 "New minor cyclic peptides from *Brachystemma calycinum*".

Cheng Y-X, Zhou J, Teng R-W and Tan N-H (2002) Acta Botanica Yunnanica 23(4): 527-530 "Nitrogen-containing compounds from *Brachystemma calycinum*".

Cheng YX, Zhou J, Tan NH, Teng RW, Lu Y, Wang C and Zheng QT (2002) Journal of Natural Products 65(5): 750-2 "Isolation and characterization of Brachystemidines A-E, novel alkaloids from *Brachystemma calycinum*."

*Primary Examiner*—Christopher R. Tate
*Assistant Examiner*—Melenie McCormick
(74) *Attorney, Agent, or Firm*—Eagle IP Limited; Jacqueline C. Lui

(57) ABSTRACT

The present invention is an extract of the herb *Brachystemma calycinum* for the amelioration or treatment of pain or discomfort due to, or associated with, osteoarthritis. The extract is obtained by a multi-step extraction process wherein the temperatures of each step never reaches boiling point.

21 Claims, 3 Drawing Sheets

HERBAL PREPARATION FOR JOINTS

FIELD OF INVENTION

The present invention is related in general to the field of over-the-counter dietary and health supplements, and botanical products. In particular, the present invention relates to a herbal extract for the amelioration or treatment of pain or discomfort due to, or associated with, osteoarthritis.

BACKGROUND OF INVENTION

References which are cited in the present disclosure are not necessarily prior art and therefore their citation does not constitute an admission that such references are prior art in any jurisdiction.

The herb *Brachystemma calycinum* D. Don (*B. calycinum*) is a plant indigenous to southern-western China, the Himalayas and its habitat range extends as far south as South-East Asia. In China, the herb is known as "duanfan hua". The herb is relatively unknown to the scientific community and very little of it outside of the plant systematics and taxonomic literature has been published.

In 2001, a paper describing four minor cyclic peptides isolated from ethanolic extracts from this plant was published (Cheng et al). In 2002, Cheng et al isolated five nitrogen-containing compounds from an ethanol extract of the herb. Five novel alkaloids were also isolated from the roots of the herb by Cheng et al.

It is an object of the present invention to teach a method of preparing a useful extract of this herb.

SUMMARY OF INVENTION

One aspect of the present invention is the method of preparing the extract of the herb *Brachystemma calycinum*. The method of the present invention generally comprises providing the herb, acidifying the herb in a suitable acid, decocting the herb in a suitable liquid, filtering the decoction and concentrating the decoction to obtain the herbal extract which is the second aspect of the present invention.

More specifically, the preferred embodiment of the present invention comprises providing the dried herb, acidifying the dried herb by soaking it in rice vinegar, heating the acid-soaked herb to dryness, and decocting the herb in water with animal bone, preferably pork bone, repeating the decoction, combining the filtrates from these two decoctions, and concentrating the filtrates to form an extract. The herbal extract may then be further process to render it more suitable for oral administration.

Another aspect of the present invention is the application of a therapeutically effective amount of an extract of *Brachystemma calycinum* prepared by the method taught for the amelioration of joint injury and discomfort due to, or associated with, osteoarthritis. This application may be for prophylaxis or for therapy of the complaint.

Yet another aspect of the present invention is the use of an extract of *Brachystemma calycinum* in the manufacture of a medicament for the therapeutic and/or prophylactic treatment of osteoarthritis, or joint paint or discomfort.

Still yet another aspect of the present invention is a formulation for the treatment of osteoarthritis, the formulation comprising an extract of the acidified herb *Brachystemma calycinum*.

The present invention can also be used as a health or nutritional supplement.

DETAILED DESCRIPTION

Figure 1:
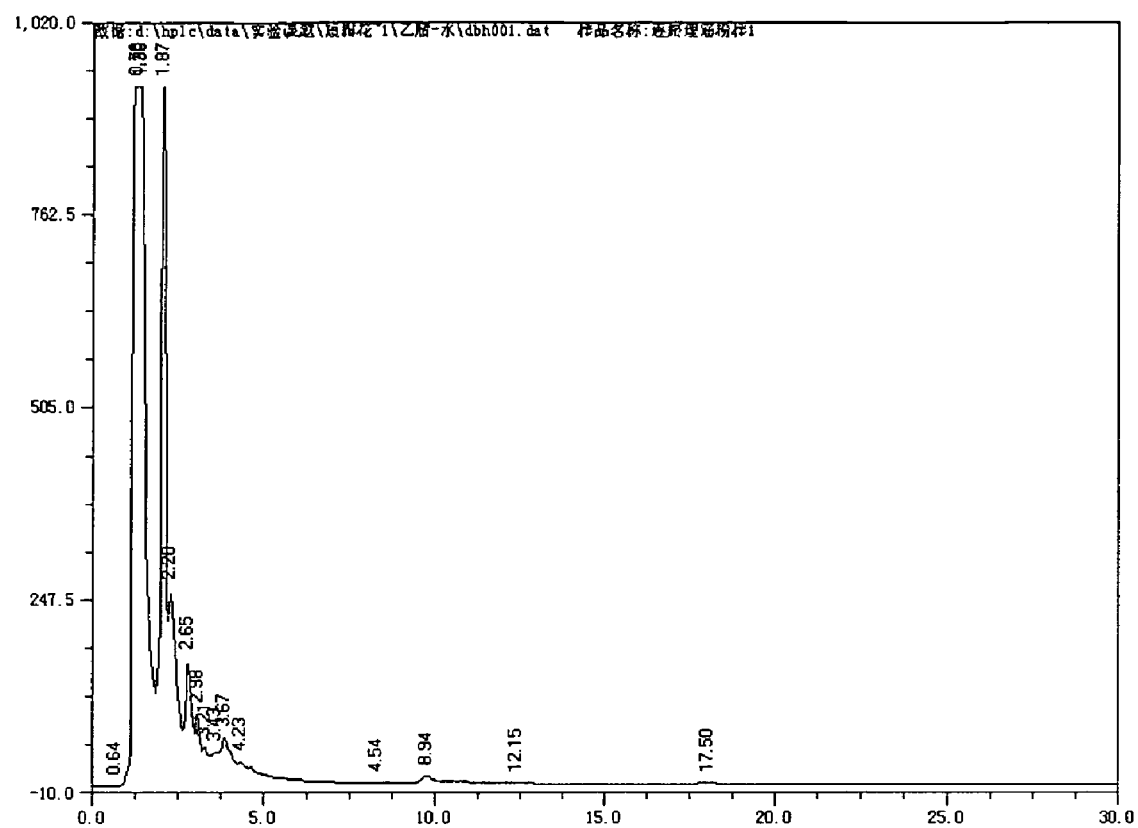
FIG. 1 is the HPLC chromatogram for the extract prepared as an aqueous sample for HPLC analysis.

As used in the present specification and claims, the terms "comprise," "comprises," and "comprising" mean "including, but not necessarily limited to". For example, a method, apparatus, molecule or other item which contains A, B, and C may be accurately said to comprise A and B. Likewise, a method, apparatus, molecule or other item which "comprises A and B" may include any number of additional steps, components, atoms or other items as well.

Also, unless otherwise defined, all technical and scientific terms used herein have the same meaning as commonly understood by one of ordinary skill in the art of traditional Chinese medicine (TCM) to which this invention belongs. Although any methods or materials similar to those described herein can be used in the practice or testing of the present invention, only the preferred embodiment is described. Utilizing the description below, a person skilled in the art of the preparation and use of Chinese herbal medicine can readily practice the methods of the claimed invention.

While dried material is traditionally used and preferred in Chinese herbal medicine, it must be recognized that drying of plant materials facilitates their storage, transportation and subsequent processing. Drying may not be a requirement to derive the benefits of these herbs. As such, it is understood that the present invention may be practiced with the corresponding quantity of the fresh plant material as well. The use of fresh plant material, sufficient to meet the requisite quantity and proportions of the extract used, come under the scope of the present claims.

A person skilled in the art will appreciate that it is possible, with plant cell and tissue culture techniques, to culture the cells and tissue of this herb in vitro and to extract any active components of interest from these cells and tissue. Thus, while the extraction of active components from dried plant parts is preferable and taught, the extraction of these components of this herb from plant cells and tissue in culture remain within the scope and spirit of the present claims.

The techniques taught include reducing the size of the plant material during processing. Here, the reducing process may be achieved by a number of ways including, but not limited to, cutting, chopping, mincing, pounding, pulverizing, macerating, milling and grinding. While one preferred way may be taught, other ways and means of achieving a reduction in size of the materials may also be used.

As such, these methods and materials fall within the scope of the appended claims.

The following is an example of how the present invention may be practiced.

Provision of the Herb

For use in the method of the present invention, the herb *Brachystemma calycinum* (hereinafter referred to as *B. calycinum*). is usually collected in Yunnan province of China mainly in the spring and summer, and cleaned of soil and other foreign matter, washed and then dried. The herb may be manually or mechanically reduced in size to pieces about 10-15 mm long (for example, by cutting or chopping) to facilitate drying. Drying of the herb may be done under the sun or in a temperature-controlled kiln but the herb is preferentially dried in the shade. The provision of forced air may speed up the drying of the herb. The herb is dried until its moisture content is less than 10%. Thereafter, the herb may be further ground if desired.

Acidification of Herb

To perform the extraction, 100 kg of the dried ground herb (both aerial and underground parts) is soaked with 25 kg of Chinese rice vinegar in a suitable acid-resistant vessel, that is, a herb to vinegar ratio of 5:1 by weight. The pH value of Chinese rice vinegar typically ranges from 2.0 to 4.0. It is important to ensure that the entire mass of dried herb is evenly soaked with the vinegar. Thereafter the herb and vinegar admixture is heated to not more than 60° C., preferably in the temperature range of between 50-60° C., until the liquid of the acid has fully evaporated and the herb is again substantially dried. This typically takes a day and the herb and vinegar admixture is continually stirred and turned throughout this time to ensure even heating and drying of the herb mass. Typically, about 100 kg of acidified herb may be obtained from this step. To obtain larger quantities, the amounts of herb and vinegar can be increased accordingly or the above process repeated as needed.

Decoction

Thereafter 750 kg of the acidified herb is transferred into a percolator (Multi-Function Percolator, Model No TQX3, Changshou City Chemical Engineering Machine Manufacturing, Jiangsu Province, China) for decoction. To this amount of ground dried acidified herb, 300 kg of pork bone (preferably the washed, cleaned, drained and chopped or crushed large bones of the pelvis and long bones) are added, to achieve an acidified herb to bone ratio of 2.5:1 by weight. The contents are then evenly spread at the bottom of the percolator before 10,500 L of water is added, that is, a water to solid ratio of 10:1 by weight. The contents are allowed to stand for 1 hr before the temperature is raised to between 90-95° C. The contents are simmered at this temperature range with the liquid stirred or circulated for about 90 minutes. At no time are the contents allowed to boil. The liquid in the percolator is then decanted and filtered as a first filtrate. The filtration is done through successive sieves of increasingly finer meshes until the filtrate is substantially clear of visible particles.

Thereafter, 8,400 L of water is then added to the solid residue (a water to solid ratio of 8:1 by weight) in the percolator and the contents again simmered at between 90-95° C. for another 60 minutes with the liquid stirred or circulated. Again, the liquid in the percolator is decanted and filtered as above to obtain a second filtrate. The first and second filtrates are then combined as the decoction of the present invention.

Concentration of Decoction

The decoction is then concentrated (High Efficiency Concentrator, Model No 941, Hunan Energy-Saving Equipment Manufacturing, Hunan Province, China) under a lowered pressure of 0.06-0.075 MPa below standard atmospheric pressure and temperature at or below 65° C. until an extract with relative density is between 1.20 and 1.30 is obtained as determined from periodic sampling of the decoction during the concentration process.

Spray Drying of Liquid Extract

While the extract may then be dried by a number of methods such as vacuum drying, it is preferably spray-dried to form a powder. The inlet temperature is set at 200-220° C. and the outlet temperature is at 80-100° C. This powder may be further sifted through an 80 mesh sieve. About 100 kg of extract may be obtained from the stated amounts used by this process. The extract thus obtained is highly hygroscopic. It is stored in an air-tight container, preferably with a suitable desiccant, and at low temperature (around 4° C.) or immediately processed as taught below. The extract may be further processed or rendered into a form suitable for packing, storage or oral administration.

Characterization of the Extract by HPLC

The extract of the present invention as obtained by the process above was subjected to high performance liquid chromatography (HPLC) analysis.

For this, 2.0 g of the extract was refluxed with 30 ml of either water, 95% ethanol or ethyl acetate separately for one hour, filtered and then evaporated to dryness. To the three residues thus obtained, 10 ml of methanol were added to form three samples for analysis in a Shimadzu HPLC system.

Figure 2:
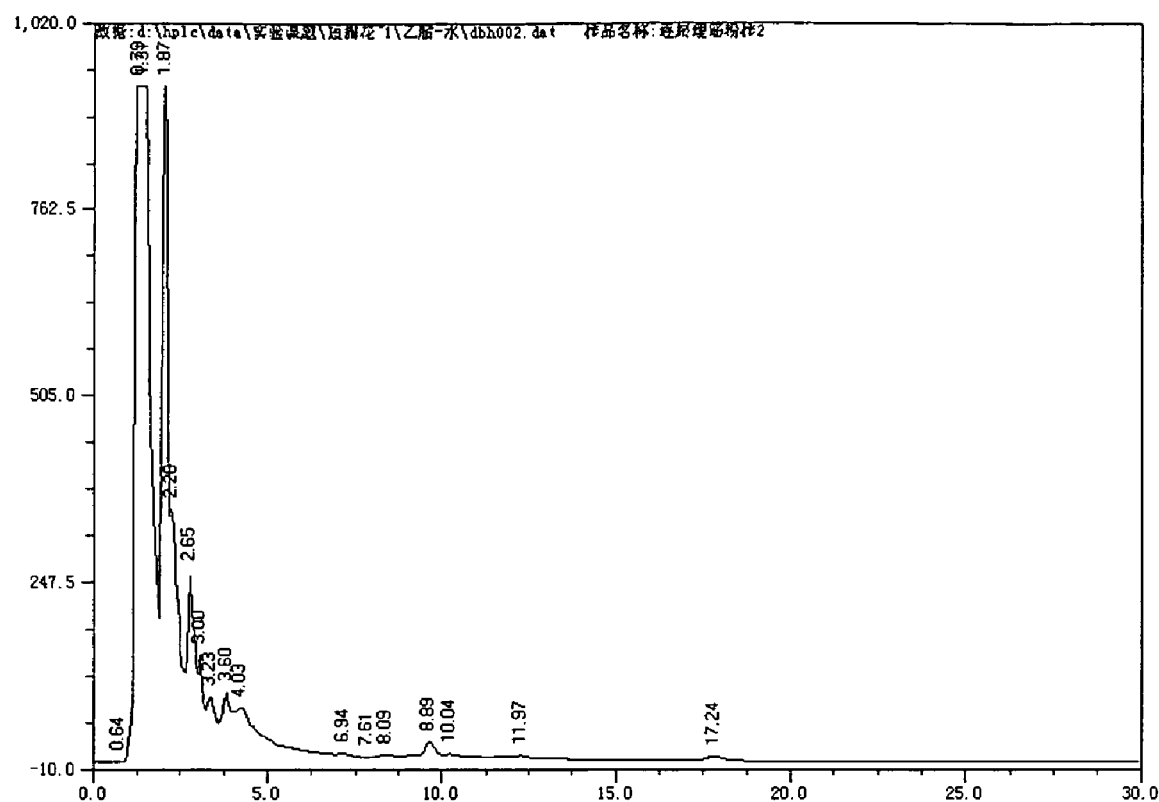
FIG. 2 is the HPLC chromatogram for the extract prepared as an ethanolic sample for HPLC analysis.
Figure 3:
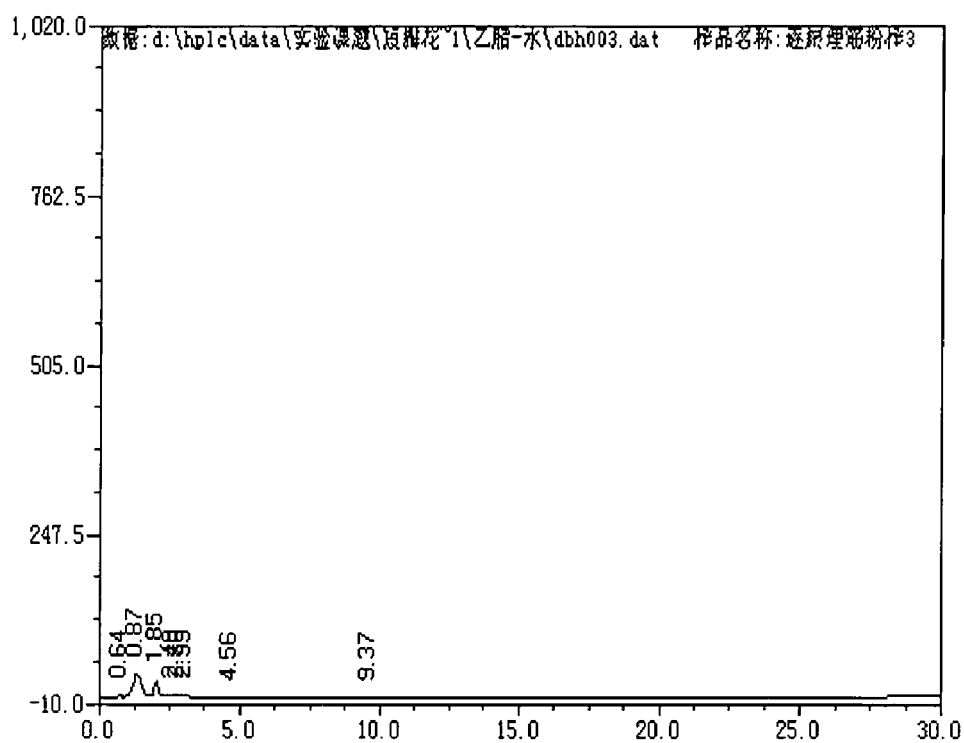
FIG. 3 is the HPLC chromatogram at one resolution for the extract refluxed with ethyl acetate for HPLC analysis.
Figure 4:
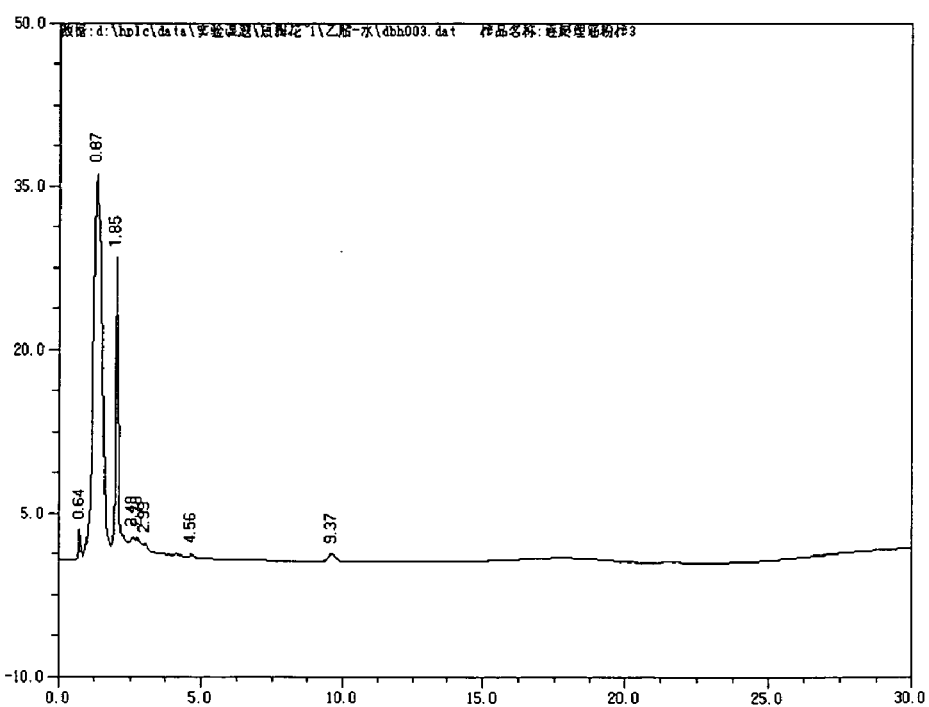
FIG. 4 is the chromatogram of FIG. 3 displayed at another resolution.

The chromatography column was 150 mm long and the matrix was octadecylsilane with chemically bonded silica as filler. The mobile phase used was acetonitrile-water mixture in a 30:70 ratio; pump flow rate was 1 ml/min and column temperature was held at 40° C. Sample detection was at 254 nm. The chromatograms obtained for the extract obtained by extraction with the three different solvents of water, ethanol and ethyl acetate are as given in FIGS. 1 to 4.

The elution profiles of the detectable components of the herbal extract invention by water, ethanol and ethyl acetate in shown as the chromatograms in FIGS. 1 to 4 are typical and characteristic for the process of the present invention. The elution profiles may be visually compared or aligned by suitable software for quality control analysis.

Quality Control Using TLC

The quality of the extract of the present invention may be ascertained by comparing prominent components of the herb *B. calycinum* with that of the invention by thin-layer chromatography (TLC) analysis as follows.

To 5 g of the extract of the present invention was added 50 ml of ethanol. The mixture was sonicated for 30 min, filtered and the filtrate evaporated to dryness to obtain a residue. This residue was dissolved in 50 ml of water and extracted three times with water-saturated n-butyl alcohol (20 ml, 15 ml and 10 ml respectively). The organic layers was then removed and pooled and re-extracted with n-butyl saturated water (20 ml, 15 ml and 10 ml respectively) and the pooled organic layers were allowed to evaporate to dryness to form a second residue. Two ml of methanol was added to dissolve this residue and the resultant solution formed the study solution.

The reference solution was obtained by adding 100 ml of water to 10 g of the dried herb which has been reduced in size to a powder. The herb powder was extracted under reflux and heat for one hour. The mixture was then filtered and evaporated to dryness to obtain a residue. Then, 100 ml of ethanol was added to dissolve the residue and the mixture was sonicated for 30 mins and filtered. The filtrate was evaporated to dryness and then dissolved in 50 ml of water. This solution was then extracted with water-saturated n-butyl alcohol (20 ml, 15 ml and 10 ml respectively). The organic layers were removed and pooled and re-extracted with n-butyl saturated water (20 ml, 15 ml and 10 ml respectively). The pooled organic layers from this second extraction were allowed to evaporate to dryness to form another residue. Two ml of methanol was added to dissolve this residue and the resultant solution formed the reference solution.

Thereafter, 50 µl each of the study and reference solutions were spotted onto a plate of silica gel G. Separation of the major components was performed using petroleum ether: ethyl formate:formic acid:water (25:5:0.5:0.5) as the mobile phase at 30-60° C. After air-drying, the chromatograph was visualized under ultra-violet light (254 nm and 365 nm). Yellow-green fluorescent spots with the same Rf values may be seen for both solutions indicating that the major components were present for the two solutions.

Optional further Processing of Extract

For the processing or rendering for oral administration, the preferred form of the extract is a capsule with suitable excipients. In one implementation, Dextrin, soluble starch and aspartame as excipients are mixed with the herb extract in a mixer. Sufficient liquid ethanol (75%) is added as a binder. This admixture mixed well and then vacuum dried in a dryer (Vacuum Dryer Model No FZGX 15-00, Wuhan Pharmaceutical Machinery Manufacturing, Hunan Province, China).

The admixture is then granulated by comminution in a (Wet Granulator Model No GHL-120, China Harbin High Technology Company, Heilongjiang Province, China) through aperture number 80 sieves to obtain a fine powder. Talcum powder may be added to improve flowability before size 1 capsules are filled with the extract powder for oral administration. The unpackaged extract was used for the animal studies while the extract in capsules were given to human patients for the clinical observations described below.

In another implementation, the extract obtained from the first implementation is further mixed with one or more ingredients to obtain a formulation. These ingredients may comprise the Chinese herbs *Ganoderma*, *Radix Angelicae Pubescentis*, *Poria*, and *Radix Gentianae Macrophyllae*.

Animal Studies

The following studies on rats measured parameters such as weight gain, appetite, blood test panel (cells and biochemical markers), visceral weight change, as well as observations from pathological and histological examination.

Animals

Healthy Sprague-Dawley rats of both genders of between 57-72 g were obtained from Guangdong Provincial Medical Experiment Animal Center. The animals fed standard grain feed provided by their source center.

Experimental Design

Healthy animals were divided randomly into four groups of 15 male and 15 female animals. Within the groups, animals were segregated in separate cages by gender. These four groups were control (distilled water), low dose (1.51 g/kg body weight), mid dose (3.01 g/kg body weight) and high dose (6.03 g/kg body weight). These doses are the equivalent of 12.5×, 25× and 50× the clinical dose for humans by surface area and 66.6×, 133.3× and 266.7× by weight. The human clinical dose was the equivalent of three capsules a day or 1.35 g.

Over a 90 day period, these 120 animals were fed either distilled water or the dose of the herbal extract in water by gavage daily according to their experimental group. Each week, the animals were individually weighed and the amount of feed consumed noted. The doses were then adjusted accordingly to administer 1.0 ml of extract per 100 g body weight.

After 90 days, 10 male and 10 females from each group were sacrificed for analysis while experimental and control treatments (as applicable) were stopped for all the remaining animals for a 30-day recovery period.

General Observations

During the experimental and recovery periods, the animals' appetite, general activity and stools were observed.

Experimental Data and Observations

Food Utilization

The mean net weight gain, total food ingestion and food utilization rate during the 90-day administration period are given in Table 1 below.

TABLE 1

Net weight gain, total food ingestion and food utilization rate during the administration period ($x \pm s$, n = 15)

| Sex | Dose (g/kg) | Net Weight Gain (g/rat) | Total Food Ingestion (g/rat) | Food Utilization (%) |
|---|---|---|---|---|
| Male | 0.00 | 455.4 ± 46.3 | 2412.7 ± 35.6 | 20.6 ± 11.5 |
|  | 1.51 | 436.5 ± 45.6 | 2385.8 ± 34.7 | 19.8 ± 12.1 |
|  | 3.01 | 409.0 ± 39.4 | 2243.3 ± 27.5 | 19.5 ± 11.5 |
|  | 6.03 | 390.0 ± 37.7 | 2211.3 ± 28.4 | 19.0 ± 11.4 |
| Female | 0.00 | 251.9 ± 34.7 | 1988.7 ± 30.7 | 14.1 ± 12.9 |
|  | 1.51 | 256.4 ± 25.5 | 1986.7 ± 24.2 | 14.1 ± 11.0 |
|  | 3.01 | 254.7 ± 33.7 | 1901.8 ± 28.2 | 14.6 ± 11.1 |
|  | 6.03 | 248.1 ± 24.4 | 1687.9 ± 14.3 | 14.7 ± 11.6 |

The mean net weight gain, total food ingestion and food utilization rate during the 30-day recovery period are given in Table 2 below.

TABLE 2

Mean net weight gain, total food ingestion and food utilization rate during the 30-day recovery period ($x \pm s$, n = 5)

| Sex | Dose (g/kg) | Net Weight Gain (g/rat) | Total Food Ingestion (g/rat) | Food Utilization (%) |
|---|---|---|---|---|
| Male | 0.00 | 75.4 ± 12.9 | 1524.4 ± 58.4 | 4.7 ± 3.5 |
|  | 1.51 | 81.2 ± 41.2 | 1569.6 ± 63.5 | 5.2 ± 2.5 |
|  | 3.01 | 82.0 ± 50.8 | 1564.0 ± 81.5 | 5.2 ± 1.8 |
|  | 6.03 | 65.4 ± 23.8 | 1487.8 ± 76.1 | 4.1 ± 2.9 |
| Female | 0.00 | 18.6 ± 17.2 | 961.0 ± 50.3 | 2.0 ± 1.0 |
|  | 1.51 | 20.4 ± 18.4 | 1021.0 ± 55.3 | 2.1 ± 0.8 |
|  | 3.01 | 20.6 ± 7.4 | 1041.3 ± 56.7 | 1.9 ± 0.8 |
|  | 6.03 | 16.2 ± 3.7 | 952.6 ± 52.9 | 1.8 ± 1.4 |

Blood Panel

After the administration period and the recovery period, a routine blood test on a panel of common markers was conducted. Blood drawn was analyzed by a Beckman 5 dif blood cell analyzer. The panel of markers comprised white blood cells (WBC) count, leukocyte classification, red blood cell (RBC) count, hemoglobin (Hb) determination, platelet (PLT) counts and hematocrit (HCT). Results for at the end of the administration period are given in Table 3 and at the end of the recovery period in Table 4 respectively.

TABLE 3

Blood markers during administration period (x ± s, n = 10)

| Sex | Dose (g/kg) | WBC (×10⁹/L) | RBC (×10¹²/L) | Hb (g/l) | PLT (×10⁹/L) | HCT (L/L) |
|---|---|---|---|---|---|---|
| Male | 0.00 | 9.9 ± 3.7 | 8.6 ± 0.5 | 158.4 ± 8.4 | 693 ± 90 | 0.47 ± 0.02 |
|  | 1.51 | 11.4 ± 3.1 | 7.7 ± 2.8 | 161.6 ± 19.8 | 724 ± 108 | 0.48 ± 0.01 |
|  | 3.01 | 12.0 ± 2.1 | 8.4 ± 0.3 | 153.0 ± 4.9 | 737 ± 125 | 0.45 ± 0.01 |
|  | 6.03 | 9.9 ± 1.5 | 7.8 ± 1.4 | 146.4 ± 5.2 | 697 ± 93 | 0.44 ± 0.02 |
| Female | 0.00 | 6.4 ± 1.1 | 8.3 ± 0.5 | 158.5 ± 6.5 | 770 ± 106 | 0.46 ± 0.02 |
|  | 1.51 | 7.2 ± 1.4 | 8.2 ± 0.2 | 154.2 ± 5.8 | 786 ± 95 | 0.44 ± 0.02 |
|  | 3.01 | 8.5 ± 2.8 | 7.7 ± 0.4 | 148.9 ± 6.2 | 711 ± 121 | 0.44 ± 0.02 |
|  | 6.03 | 7.3 ± 2.0 | 7.8 ± 0.9 | 148.9 ± 11.3 | 736 ± 161 | 0.45 ± 0.04 |

TABLE 4

Blood markers during recovery period (x ± s, n = 5)

| Sex | Dose (g/kg) | WBC (×10⁹/L) | RBC (×10¹²/L) | Hb (g/l) | PLT (×10⁹/L) | HCT (L/L) |
|---|---|---|---|---|---|---|
| Male | 0.00 | 10.8 ± 3.0 | 8.5 ± 1.1 | 159.5 ± 10.8 | 766 ± 89 | 0.43 ± 0.03 |
|  | 1.51 | 10.5 ± 1.2 | 8.8 ± 0.1 | 163.1 ± 3.4 | 740 ± 48 | 0.45 ± 0.01 |
|  | 3.01 | 12.0 ± 2.2 | 9.2 ± 0.2 | 162.4 ± 3.8 | 911 ± 60 | 0.44 ± 0.01 |
|  | 6.03 | 9.8 ± 2.8 | 8.8 ± 0.2 | 162.9 ± 3.9 | 757 ± 68 | 0.44 ± 0.01 |
| Female | 0.00 | 7.3 ± 2.6 | 8.2 ± 0.6 | 152.8 ± 5.0 | 770 ± 106 | 0.41 ± 0.01 |
|  | 1.51 | 6.6 ± 0.5 | 8.4 ± 0.5 | 158.5 ± 6.2 | 786 ± 95 | 0.42 ± 0.02 |
|  | 3.01 | 6.8 ± 2.9 | 8.0 ± 0.9 | 153.6 ± 16.8 | 711 ± 121 | 0.40 ± 0.04 |
|  | 6.03 | 8.3 ± 1.80 | 8.0 ± 0.4 | 149.5 ± 10.7 | 736 ± 161 | 0.40 ± 0.03 |

Blood Biochemistry

The blood biochemical markers measured include alanine aminotransferase (ALT), aspartate aminotransferase (AST), blood urea nitrogen (BUN), creatine (Crea), total protein (TP), albumin (ALB), total cholesterol (T-cho), blood glucose (GLu), alkaline phosphatase (ALP), total bilirubin (TBIL). These markers were examined using a Beckman CX5 automatic biological analysis instrument. The data are shown on Table 5 for the administration period and on Table 6 for the recovery period.

TABLE 5

Blood biochemical markers during administration period (x ± s)

| Sex | Dose (g/kg) | ALT (u/l) | AST (u/l) | BUN (mmol/L) | TP (g/l) | ALB (g/l) | Crea (umol/L) |
|---|---|---|---|---|---|---|---|
| Male | 0.00 | 70.9 ± 7.7 | 218.5 ± 36.3 | 9.0 ± 0.5 | 74.2 ± 3.4 | 37.0 ± 1.4 | 104.0 ± 22.2 |
|  | 1.51 | 71.2 ± 9.7 | 184.9 ± 29.6 | 8.0 ± 0.5 | 72.6 ± 4.2 | 36.9 ± 2.0 | 97.5 ± 32.3 |
|  | 3.01 | 71.7 ± 10.7 | 193.1 ± 34.2 | 7.5 ± 0.6 | 76.4 ± 3.2 | 36.4 ± 0.8 | 78.5 ± 32.0 |
|  | 6.03 | 69.7 ± 8.4 | 202.3 ± 31.7 | 7.7 ± 0.6 | 75.6 ± 3.3 | 37.3 ± 1.0 | 87.3 ± 31.2 |
| Female | 0.00 | 71.7 ± 8.4 | 199.3 ± 38.6 | 9.8 ± 2.1 | 74.6 ± 5.0 | 37.1 ± 3.0 | 116.6 ± 33.4 |
|  | 1.51 | 66.5 ± 7.4 | 172.1 ± 30.4 | 9.0 ± 1.2 | 78.7 ± 6.1 | 39.0 ± 1.8 | 96.6 ± 33.6 |
|  | 3.01 | 71.4 ± 7.4 | 168.4 ± 24.4 | 8.4 ± 1.2 | 79.5 ± 4.3 | 38.7 ± 1.6 | 115.6 ± 16.8 |
|  | 6.03 | 63.9 ± 8.0 | 201.6 ± 26.2 | 8.0 ± 1.0 | 81.3 ± 4.0 | 39.2 ± 1.7 | 96.9 ± 17.4 |

TABLE 6

Blood biochemical markers during recovery period (x ± s)

| Sex | Dose (g/kg) | Tcho (mmol/L) | Glu (mmol/L) | ALP (IU/L) | TBIL (u mol/L) |
|---|---|---|---|---|---|
| Male | 0.00 | 1.5 ± 0.3 | 6.6 ± 0.6 | 235.1 ± 34.4 | 34.8 ± 7.4 |
|  | 1.51 | 1.6 ± 0.3 | 6.3 ± 0.5 | 223.6 ± 37.7 | 34.9 ± 14.3 |
|  | 3.01 | 1.5 ± 0.2 | 7.4 ± 1.0 | 241.7 ± 28.0 | 25.8 ± 14.9 |
|  | 6.03 | 1.4 ± 0.2 | 7.8 ± 1.0 | 229.9 ± 25.8 | 45.3 ± 20.8 |
| Female | 0.00 | 1.6 ± 0.4 | 7.8 ± 1.3 | 216.6 ± 54.6 | 22.7 ± 7.0 |
|  | 1.51 | 1.7 ± 0.2 | 7.1 ± 0.7 | 216.9 ± 50.6 | 25.0 ± 4.4 |

TABLE 6-continued

Blood biochemical markers during recovery period (x ± s)

| Sex | Dose (g/kg) | Tcho (mmol/L) | Glu (mmol/L) | ALP (IU/L) | TBIL (u mol/L) |
|---|---|---|---|---|---|
| | 3.01 | 2.1 ± 0.2 | 7.3 ± 0.6 | 226.7 ± 49.0 | 24.9 ± 11.2 |
| | 6.03 | 1.8 ± 0.3 | 7.6 ± 0.6 | 205.0 ± 39.0 | 31.1 ± 8.3 |

Viscera Examination

At the end of the each period (administration and recovery), the animals were sacrificed and organs (liver, kidney, heart, lung, spleen, brain, adrenal gland, prostate gland, and testicle or uterus) were removed, weighed and examined for any signs of overt pathology. The organs and their weights are given in Table 7 for the administration period and in Table 8 for the recovery period.

Histology

Following gross visual examination, tissue from the organs from animals in the control and high dose groups were processed by standard histological techniques for microscopic examination. The organ tissues were fixed in formalin, embedded in paraffin, sectioned with a microtome and mounted on glass slides, stained with hematoxylin and eosin (H&E) before being examined. No gross pathology was observed by the naked eye. As such, only histological specimens from the control and high-dose groups were subjected to examination under the microscope. The observations are as follows.

Liver: It was observed under the microscope that the liver membrane was intact, with no increase in thickness. No hydropic degeneration, fatty change and necrosis were seen in hepatocytes. There was no cholestasis noted in the hepatocytes and in the bile duct. No dilatation of the sphincter and no exudation were noted.

TABLE 7

Viscera weight at end of administration period (g, x ± s, n = 10)

| Sex | Dose (g/kg) | Heart | Liver | Spleen | Lung | Kidney |
|---|---|---|---|---|---|---|
| Male | 0.00 | 1.59 ± 0.23 | 17.6 ± 1.9 | 0.83 ± 0.16 | 2.29 ± 0.66 | 2.97 ± 0.40 |
| | 1.51 | 1.50 ± 0.19 | 17.2 ± 2.3 | 0.96 ± 0.12 | 2.46 ± 0.48 | 2.93 ± 0.30 |
| | 3.01 | 1.55 ± 0.19 | 15.4 ± 1.9 | 0.87 ± 0.19 | 2.53 ± 0.64 | 3.00 ± 0.32 |
| | 6.03 | 1.49 ± 0.19 | 16.4 ± 1.3 | 0.88 ± 0.15 | 2.35 ± 0.37 | 3.10 ± 0.35 |
| Female | 0.00 | 1.09 ± 0.10 | 9.6 ± 1.7 | 0.59 ± 0.11 | 1.91 ± 0.25 | 1.99 ± 0.23 |
| | 1.51 | 1.06 ± 0.08 | 10.2 ± 1.0 | 0.62 ± 0.11 | 1.86 ± 0.32 | 2.03 ± 0.20 |
| | 3.01 | 1.10 ± 0.19 | 10.1 ± 1.7 | 0.79 ± 0.28 | 1.90 ± 0.27 | 1.97 ± 0.23 |
| | 6.03 | 1.05 ± 0.11 | 3.22 ± 1.0 | 0.66 ± 0.10 | 1.92 ± 0.39 | 2.09 ± 0.16 |

| Sex | Dose (g/kg) | Brain | Adrenal gland | Prostate gland | Testicle | Uterus |
|---|---|---|---|---|---|---|
| Male | 0.00 | 1.96 ± 0.16 | 0.10 ± 0.03 | 0.62 ± 0.12 | 3.54 ± 0.18 | |
| | 1.51 | 1.94 ± 0.14 | 0.10 ± 0.02 | 0.68 ± 0.20 | 3.52 ± 0.29 | |
| | 3.01 | 2.00 ± 0.20 | 0.10 ± 0.03 | 0.66 ± 0.20 | 3.52 ± 0.30 | |
| | 6.03 | 1.97 ± 0.13 | 0.10 ± 0.04 | 0.66 ± 0.22 | 3.59 ± 0.35 | |
| Female | 0.00 | 1.65 ± 0.27 | 0.12 ± 0.03 | | | 0.22 ± 0.09 |
| | 1.51 | 1.63 ± 0.34 | 0.10 ± 0.02 | | | 0.18 ± 0.08 |
| | 3.01 | 1.89 ± 0.11 | 0.10 ± 0.02 | | | 0.20 ± 0.07 |
| | 6.03 | 1.91 ± 0.10 | 0.11 ± 0.03 | | | 0.23 ± 0.09 |

TABLE 8

Viscera weight at end of recovery period (g, x ± s, n = 5)

| Sex | Dose (g/kg) | Heart | Liver | Spleen | Lung | Kidney |
|---|---|---|---|---|---|---|
| Male | 0.00 | 1.65 ± 0.22 | 20.5 ± 5.7 | 1.09 ± 0.92 | 2.52 ± 1.10 | 3.08 ± 0.62 |
| | 1.51 | 1.67 ± 0.30 | 20.3 ± 5.2 | 0.89 ± 0.14 | 2.44 ± 0.59 | 3.22 ± 0.64 |
| | 3.01 | 1.48 ± 0.18 | 18.6 ± 3.2 | 1.02 ± 0.24 | 2.51 ± 0.46 | 3.10 ± 0.35 |
| | 6.03 | 1.53 ± 0.05 | 17.5 ± 1.4 | 0.98 ± 0.10 | 2.26 ± 0.54 | 2.64 ± 0.11 |
| Female | 0.00 | 1.02 ± 0.16 | 11.2 ± 1.6 | 0.72 ± 0.19 | 1.96 ± 0.70 | 1.87 ± 0.27 |
| | 1.51 | 1.09 ± 0.14 | 12.2 ± 1.1 | 0.71 ± 0.09 | 2.24 ± 0.61 | 2.01 ± 0.06 |
| | 3.01 | 1.13 ± 0.08 | 11.9 ± 0.4 | 0.99 ± 0.40 | 1.84 ± 0.14 | 2.20 ± 0.16 |
| | 6.03 | 0.98 ± 0.08 | 10.1 ± 0.4 | 0.72 ± 0.10 | 1.72 ± 0.28 | 2.01 ± 0.22 |

| Sex | Dose (g/kg) | Brain | Adrenal gland | Prostate gland | Testicle | Uterus |
|---|---|---|---|---|---|---|
| Male | 0.00 | 2.04 ± 0.32 | 0.08 ± 0.02 | 1.15 ± 0.08 | 3.65 ± 0.22 | |
| | 1.51 | 2.03 ± 0.28 | 0.07 ± 0.03 | 0.97 ± 0.06 | 3.88 ± 0.20 | |
| | 3.01 | 1.84 ± 0.27 | 0.09 ± 0.04 | 0.76 ± 0.34 | 3.69 ± 0.37 | |
| | 6.03 | 1.81 ± 0.29 | 0.08 ± 0.02 | 1.09 ± 0.27 | 3.33 ± 0.50 | |
| Female | 0.00 | 1.65 ± 0.27 | 0.13 ± 0.04 | | | 0.21 ± 0.06 |
| | 1.51 | 1.63 ± 0.34 | 0.09 ± 0.02 | | | 0.21 ± 0.04 |
| | 3.01 | 1.89 ± 0.11 | 0.08 ± 0.01 | | | 0.18 ± 0.04 |
| | 6.03 | 1.91 ± 0.10 | 0.09 ± 0.02 | | | 0.24 ± 0.15 |

Kidney: The structure of the glomeruli was clearly intact, with no obvious edema, atrophy or fibrosis. No obvious edema in distal and proximal tubules, no fatty change, hyaline change or necrosis was noted. The basement membrane was intact. No casts seen in collecting tubules.

Heart: The pericardium was intact, with no hyperplasia of the connective tissue. No myocardial fiber hyperplasia or atrophy in the myocardium was noted. The myocardial fibers were well arranged with no rupture, necrosis or scarring. No edema was found in myocardial cells. Endocardial cells were intact, with no infarct changes or evidence of thrombi.

Spleen: No hyperplasia of fibrous connective tissue seen in the spleen membrane and spleen cords. No obvious inflammatory cell infiltration, no reactive hyperplasia in splenic sinuses. No stagnant blood and inflammatory cell exudates noted in the red pulp.

Brain: No infiltration noted on the surface of the brain. The structure of white and grey matter was clear. The neurons had not changed or become necrotic. No hemorrhage, inflammation or abnormality was found in the interstitia.

Stomach and intestines: The mucous membrane surface was smooth, and the color was normal. No abnormal exudate, bleeding, necrosis or ulceration was found. The structure of the intestines and stomach was intact, and the superficial mucosa of the gastric membrane was intact. Glands were well arranged. No epithelial detachment, necrosis or ulcer was found. No abnormal pathological changes like hyperemia or edema was found in the submucosa.

Testicle: The outer white membrane was intact. The lobule and epidydimal cords were radially arranged. No atrophy or detachment was found in the supporting cells in the cords, the primary spermatoblasts; secondary spermatoblasts or spermatocytes.

Prostate gland: Prostatic glandular tissue structure was normal. The glandular epithelium was well arranged. No necrosis noted in the epithelium. No calculus in the gland cavity. No hyperplasia of interstitia. No inflammatory cells infiltration was observed.

Ovary: Well-structured primary ovum follicles, secondary ovum follicles and primary follicles were seen in the ovary tissue. The epidermis was intact, without any engorgement or putrescence present. Uterus: Under microscope, the uterine endometrial glands and interstitia were normal and myometrial structure was normal, without bleeding or other abnormal change.

Thyroid gland: Under the microscope, the follicular structure of thyroid gland was normal, without colloidal like deposition.

Thymus: Under microscope, the thymus structure was normal, without any unusual pathological changes.

Adrenal gland: No pleomorphic change or necrosis noted in the zona glomerulosa, reticular cells in cortex. No pathological changes in the medulla cells.

Lymph nodes: Under the microscope, cortex and medulla of the lymph nodes were normal without unusual changes.

Observations

From the above, during the administration (study) and recovery periods, compared to the control group, the main organs of the different groups of animals (heart, liver, lung, spleen, kidney, brain, stomach, intestines, thymus, thyroid gland, pancreas, adrenal gland, lymph nodes, testicle, prostate gland, ovary and uterus) were normal, without obvious pathological changes.

From the experimental data above, it was shown that the herbal extract of the present invention does not have any adverse effects on animals. From Week 10, male rats in the medium and high dose groups gained weight more slowly. This difference was statistically significant compared to the control group ($p<=0.05$). There were no other significant differences between the experimental and control groups in the other indices such as the hematological parameters, the biochemical parameters and the pathological observations. No acute or chronic toxic reactions were observed.

Clinical Observations

The extract of the present invention as packaged in capsules described above, was given to patients who complained of joint problems due to osteoarthritis as well as other joint complaints. Some notable examples are included below to illustrate the efficacy of the extract in alleviating symptoms associated with osteoarthritis, and joint pain and injury. Osteoarthritis may be distinguished from rheumatoid arthritis as follows.

Rheumatoid Arthritis

Rheumatoid arthritis (RA) is a chronic multisystem disease of unknown cause. The characteristic feature of RA is persistent inflammatory synovitis, usually involving peripheral joints in a symmetric distribution.

Epidemiology and Genetics: Family studies indicate a genetic predisposition.

Pathology and Pathogenesis: Characteristic constellation of features, which include hyperplasia and hypertrophy of the synovial lining cells; focal or segmental vascular changes, including microvascular injury, thrombosis, and neovascularization; edema; and infiltration with mononuclear cells. Rheumatoid synovium is characterized by local production of inflammatory cytokines and chemokines which account for many of the features of rheumatoid synovitis, including the synovial tissue inflammation, synovial fluid inflammation, synovial proliferation, and cartilage and bone damage, as well as the systemic manifestations of RA.

Clinical Manifestations. Characteristically, RA is a chronic polyarthritis especially those of the hands, wrists, knees, and feet. Pain, swelling, and tenderness may initially be poorly localized to the joints. Morning stiffness is almost invariable. The majority of patients will experience constitutional symptoms such as weakness, easy fatigability, anorexia, and weight loss.

Extra-articular Manifestations: These include rheumatoid nodules, rheumatoid vasculitis, pleuropulmonary manifestations, and Felty's syndrome.

Laboratory Findings: Rheumatoid factors, autoantibodies are found in more than two-thirds of adults with the disease. The erythrocyte sedimentation rate is increased in nearly all patients with active RA. In synovial fluid analysis polymorphonuclear leukocytes predominate.

Clinical Course and Prognosis: Most patients experience persistent but fluctuating disease activity.

Treatment: Disease-modifying antirheumatic drugs, immunosuppressive therapy, surgery are usually prescribed.

Osteoarthritis

Osteoarthritis (OA) represents failure of the diarthrodial (movable, synovial-lined) joint. In idiopathic (primary) OA, the most common form of the disease, no predisposing factor is apparent. Secondary OA is pathologically indistinguishable from idiopathic OA but attributable to an underlying cause which includes trauma, metabolic, endocrine factors, etc.

Epidemiology and Risk Factors: OA is the most common joint disease of humans. Age is the most powerful risk factor for OA. In women, ages of 45 to 64 years, the prevalence was 30%. Major trauma and repetitive joint use are also important risk factors for OA. Secondary OA can be classified as trauma, metabolic, endocrine, etc. Obesity is a risk factor for knee OA and hand OA. OA is a disease of an organ, the synovial joint in load-bearing areas of the articular cartilage. Joint surface thins, the cartilage softens, the integrity of the surface is breached, and vertical clefts develop.

Clinical Features: The joint pain of OA is often described as a deep ache and is localized to the involved joint. Typically, the pain of OA is aggravated by joint use and relieved by rest. Localized tenderness and bony or soft tissue swelling are often present. Bony crepitus is characteristic.

Laboratory and Radiographic Findings: Diagnosis of OA is clinical and radiographic, where joint space narrowing, subchondral bone sclerosis, subchondral cysts, and osteophytosis are seen singularly or collectively. No laboratory studies are diagnostic for OA.

Drug Therapy of OA: Therapy for OA today is palliative; no pharmacologic agent has been shown to prevent, delay the progression of, or reverse the pathologic changes of OA in humans.

The following are examples of patients treated with capsules of the herbal preparation of the present invention.

Patient A

A 17-year old female patient had trauma over the limbs and joints with limited locomotion of the knees. The patient was prescribed one capsule to be taken each day for five days. Feldene and Hirudoid were prescribed for the bruises. Her condition improved after five days and she was cured.

Patient B

A male patient, 85 years old, was diagnosed with osteoarthritis in both lower limbs and had limited locomotion and mobility accompanied by pain. He was prescribed one capsule twice a day. After 25 days, he experienced a significant decrease in pain and an increase in the smoothness when walking.

Patient C

A female patient, 80 years old, had severe arthritis of both knees. She was prescribed one capsule twice a day for 23 days. Thereafter, she showed a significant improvement in walking and experienced a decrease in pain.

Patient D

A male patient, 27 years old, presented with swelling of finger and arthritis of the interphalangeal joints and right elbow. He was prescribed the capsule three times a day for 30 days. Patient recovered fully thereafter.

Patient E

Another 17-year old female patient complained of multiple interphalangeal swelling and pain daily. She was prescribed one capsule once every two weeks for nine months. The symptoms then decreased in frequency from daily occurrences to once every two weeks or so.

Patient F

A male patient, 56-years old, had swelling and joint pain of the first interphalangeal joint. He recovered after being prescribed two capsules daily for two months.

Patient G

A female patient, age 45, was diagnosed with arthritis in her left knee and difficulty in walking. She was prescribed one capsule twice a day for four months. Thereafter, the dosage was reduced to one capsule a week for one year. The patient showed decrease in swelling and pain and had full restoration of walking ability.

Summary of Clinical Observations

From the above examples, it can be seen that the herbal extract is efficacious for the treatment of joint injuries and pain in conditions associated with osteoarthritis and other related injuries. While efficacy is seen in the application of the extract for therapy, it is envisaged that the extract may be used for the prophylaxis of these complaints as well.

It is known that osteoarthritis is almost an untreatable disease for therapy for osteoarthritis is palliative and no pharmacologic agent has been shown to be effective in preventing or delaying the progression or reversing the pathologic changes of osteoarthritis in human. This said herbal extract has been proved from the above examples that it is efficacious in alleviating the symptoms and the progression of osteoarthritis as well as restoring the function of afflicted patients. Thus, it can be envisaged that this herbal extract may be able to prevent osteoarthritis in susceptible individuals, delay the onset of clinical symptoms in patients with radiological or MRI evidence of early signs of osteoarthritis, arrest the progression of patients with clinical osteoarthritis, and reverse the pathologic changes of osteoarthritis. There is evidence that this herbal extract may also be useful for patients suffering from rheumatoid arthritis not in arresting the immunological part of rheumatoid arthritis but in helping to arrest the progression of the disease secondary to malfunction arising from the malformed joints and the stress on the cartilages caused by dysfunction. The present invention was shown to be efficacious in treating or at least alleviating the symptoms of osteoarthritis.

Variations in the Practice of the Invention

Strict Good Manufacturing Practice (GMP) standards for pharmaceutical products were followed for the above examples. This is an optional practice and not be necessary depending on the user's requirements.

While an example of how the present invention may be practiced is taught above, a person skilled in the art will also recognize that it are for illustration only and that many equivalent and alternative steps are possible in the preparation method without departing from the scope and spirit of the invention.

For example, although the entire herb is used, the various parts of the herb (stem, leaves, flowers, roots, etc) of the herb may be selected within the scope of claims. A person skilled in the art will appreciate that it is possible, with plant cell and tissue culture techniques, to culture the cells and tissue of these herbs in vitro and to extract the active components of interest from these cells and tissue. Thus, while the extraction of these active components from dried plant parts is preferable and taught, the extraction of these components from plant cells and tissue in culture are also possible.

As for the acidification step, many kinds of edible acids besides naturally fermented vinegar may be used. For example, artificially synthesized acetic acid or natural fruit juices may be used to acidify the herb. In addition, while pork bone was used in the preferred embodiment, any suitable bone from other animals such as reptiles, mammals or fish may be used within the scope of the present invention. Additionally, a person skilled in the art will recognize that although the decoction was concentrated under reduced pressure and the extract obtained by spray drying, it is equally feasible to obtain the extract by lyophilization or freeze drying.

While the herbal extract was packaged in a capsule, other suitable methods of preparation for packaging are equally feasible. For oral administration, the extracts may be provided as a tablet, aqueous or oil suspension, dispersible powder or granule, emulsion, hard or soft capsule, syrup, elixir, or beverage. Compositions intended for oral use may be prepared according to any method known in the art for the manufacture of pharmaceutically acceptable compositions and such compositions may contain one or more of the following agents: sweeteners, flavoring agents, coloring agents and preservatives. The sweetening and flavoring agents will increase the palatability of the preparation. Capsules containing extracts in admixture with non-toxic pharmaceutically acceptable agents or excipients suitable for capsules manufacture are acceptable. That the agents are "pharmaceutically acceptable" means that the agents should be acceptable in the sense of being compatible with the other ingredients of the formulation (as well as non-injurious to the patient). Such excipients include inert diluents such as calcium carbonate, sodium carbonate, lactose, calcium phosphate or sodium phosphate; granulating and disintegrating agents, such as corn starch or alginic acid; binding agents such as starch, gelatin or acacia; and lubricating agents such as magnesium stearate, stearic acid or talc. Tablets may be uncoated or may be coated by known techniques to delay disintegration and absorption in the gastrointestinal tract and thereby provide a sustained action over a longer period of time. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil. In some embodiments, aqueous suspensions may contain an extract of the invention in admixture with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

Oil suspensions may be formulated by suspending the active ingredient in a vegetable oil, such as arachis oil, olive oil, sesame oil or coconut oil, or in a mineral oil such as liquid paraffin. The oil suspension may contain a thickening agent, such as beeswax, hard paraffin or cetyl alcohol. Sweetening agents, such as those set forth above, and flavoring agents may be added to provide a palatable oral preparation. These compositions may be preserved by an added antioxidant such as ascorbic acid. Dispersible powders and granules of the invention suitable for preparation of an aqueous suspension by the addition of water provide one or more extracts in admixture with a dispersing or wetting agent, a suspending agent, and one or more preservatives. Additional excipients, for example sweetening, flavoring and coloring agents, may also be present.

Syrups and elixirs may be formulated with sweetening agents, such as glycerol, sorbitol or sucrose. Such formulations may also contain a demulcent, a preservative, a flavoring or a coloring agent.

While oral administration is preferred, other methods of administering the extract of the present invention is not precluded. The extract preparations for parenteral administration may be in the form of a sterile injectable preparation, such as a sterile injectable aqueous or oleaginous suspension. This suspension may be formulated according to methods well known in the art using suitable dispersing or wetting agents and suspending agents. The sterile injectable preparation may also be a sterile injectable solution or suspension in a non-toxic parenterally-acceptable diluent or solvent, such as a solution in 1,3-butanediol. Suitable diluents include, for example, water, Ringer's solution and isotonic sodium chloride solution. In addition, sterile fixed oils may be employed conventionally as a solvent or suspending medium. For this purpose, any bland fixed oil may be employed including synthetic mono or diglycerides. In addition, fatty acids such as oleic acid may likewise be used in the preparation of injectable preparations.

The pharmaceutical compositions may also be in the form of oil-in-water emulsions. The oily phase may be a vegetable oil, such as olive oil or arachis oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions may also contain sweetening and flavoring agents.

The amount of extract that may be combined with the carrier material to produce a single dosage form will vary depending upon the patient treated and the particular mode of administration.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit and scope of that which is described and claimed.

REFERENCES

1. Cheng Y-X, Zhou J and Tan N—H (2001) Journal of Integrative Plant Biology (Acta Botanica Sinica) 43(7): 760-765 New minor cyclic peptides from *Brachystemma calycinum*.
2. Cheng Y-X, Zhou J, Teng R-W and Tan N—H (2001) Acta Botanica Yunnanica 23(4): 527-530 Nitrogen-containing compounds from *Brachystemma calycinum*.
3. Cheng Y X, Zhou J, Tan N H, Teng R W, Lu Y, Wang C and Zheng Q T (2002) Journal of Natural Products 65(5): 750-2 Isolation and characterization of Brachystemidines A-E, novel alkaloids from *Brachystemma calycinum*.

What is claimed is:

1. An herbal extract obtained by a process comprising providing the herb *Brachystemma calycinum*;
   acidifying the herb;
   decocting the acidified herb in a liquid to obtain a decoction; and
   concentrating the decoction to obtain the extract.

2. The herbal extract according to claim 1, wherein the acidifying step comprises
   soaking the herb with vinegar to form an admixture; and
   heating and stirring the admixture at a temperature of not more than 60° C. until the admixture is substantially dry.

3. The herbal extract according to claim 1, wherein the decocting step comprises simmering the acidified herb with animal bone in a liquid at a temperature below the liquid's boiling point.

4. The herbal extract according to claim 3, wherein the simmering comprises stirring or circulating the herb-bone-containing liquid for a sufficient period of time.

5. The herbal extract according to claim 3, wherein the animal bone comprises pork bone.

6. The herbal extract of claim 1, wherein the process further comprises filtering the decoction.

7. The herbal extract of claim 1, wherein the concentrating step is performed under a pressure below standard atmospheric pressure.

8. The herbal extract of claim 1, wherein the process further comprises drying the concentrated extract by vacuum drying or spray drying.

9. The herbal extract of claim 1, wherein the process further comprises mixing the concentrated extract with a suitable excipient.

10. The herbal extract of claim 8, wherein the drying is performed in the presence of a suitable excipient.

11. The herbal extract of claim 1, wherein the process further comprises processing the extract into a form suitable for oral administration.

12. The herbal extract of claim 11, wherein the form suitable for oral administration comprises a capsule.

13. The herbal extract of claim 1, wherein the process further comprises adding to the extract an ingredient selected from the herbs *Ganoderma, Radix Angelicae Pubescentis, Poria* or *Radix Gentianae Macrophyllae*.

14. A method for ameliorating symptoms of osteoarthritis, comprising administering to a subject in need thereof a therapeutically effective amount of the extract of claim 1.

15. A formulation for ameliorating symptoms of osteoarthritis, comprising a therapeutically effective amount of the extract of claim 1.

16. A method for the amelioration or treatment of pain or discomfort due to, or associated with, osteoarthritis, comprising administering to a subject in need thereof a medicament comprising a therapeutically effective amount of the extract according to claim 1.

17. The method of claim 16, wherein the medicament further comprises an ingredient selected from the herbs *Ganoderma, Radix Angelicae Pubescentis, Poria* or *Radix Gentianae Macrophyllae*.

18. The herbal extract of claim 2, wherein the heating temperature is 50 to 60° C.

19. A process for preparing the extract of claim 1, comprising
providing the herb *Brachystemma calycinum;*
acidifying the herb;
decocting the acidified herb in a liquid to obtain a decoction; and
concentrating the decoction to obtain the extract.

20. The process of claim 19, wherein the acidifying comprises
soaking the herb with vinegar to form an admixture; and
heating and stirring the admixture at a temperature of not more than 60° C. until the admixture is substantially dry; and wherein
the decocting step comprises
simmering the acidified herb with animal bone in a liquid at a temperature below its boiling point by stirring or circulating the herb-bone-containing liquid for a sufficient period of time to obtain a decoction; and
filtering the decoction; and wherein
the concentrating step comprises
concentrating the decoction to obtain the extract at a lowered pressure;
drying the concentrated extract in the presence of a suitable excipient; and
processing the extract into a form suitable for oral administration to obtain the formulation.

21. The process of claim 20, wherein the concentrating step comprises concentrating the decoction at a lower pressure and a temperature of 65° C. or below until the extract reaches a relative density of between 1.2 and 1.3.

* * * * *